United States Patent [19]
Girodo et al.

[11] Patent Number: 5,271,394
[45] Date of Patent: Dec. 21, 1993

[54] METHOD AND APPARATUS FOR CALCULATING THE ATRIAL ESCAPE INTERVAL FOR A CARDIAC PACING DEVICE IN THE EVENT OF ATRIAL EXTRA SYSTOLES

[75] Inventors: Sylvie Girodo, Montrouge; Odile Malherbe, Cachan, both of France

[73] Assignee: ELA Medical, Montrouge, France

[21] Appl. No.: 796,003

[22] Filed: Nov. 22, 1991

[30] Foreign Application Priority Data

Nov. 30, 1990 [FR] France .................. 90 15012

[51] Int. Cl.$^5$ .................................. A61N 1/362
[52] U.S. Cl. ........................................... 607/15
[58] Field of Search ............ 128/419.0 PG, 419.0 PT, 128/697

[56] References Cited

U.S. PATENT DOCUMENTS

| | | | |
|---|---|---|---|
| 4,421,116 | 12/1983 | Markowitz | 128/419.0 PG |
| 4,485,818 | 12/1984 | Leckrone et al. | 128/419.0 PG |
| 4,505,276 | 3/1985 | Markowitz et al. | 128/419.0 PT |
| 4,539,991 | 9/1985 | Boute et al. | 128/419.0 PG |
| 4,624,260 | 11/1986 | Baker, Jr. et al. | 128/419.0 PG |
| 4,712,554 | 12/1987 | Garson, Jr. | 128/419.0 PG |
| 4,723,551 | 2/1988 | Hedberg et al. | 128/419.0 PG |
| 4,920,965 | 5/1990 | Funke et al. | 128/419.0 PG |
| 5,027,815 | 7/1991 | Funke et al. | 128/419.0 PG |
| 5,074,308 | 12/1991 | Sholder et al. | 128/419.0 PT |

Primary Examiner—William E. Kamm
Attorney, Agent, or Firm—Davis Hoxie Faithfull & Hapgood

[57] ABSTRACT

A method for calculating the atrial escape interval. A calculation is made of the average value of the delays between two "P" waves measured over 8 heart cycles, and this average value is taken as the value of the atrial escape interval. The "P" wave is monitored to identify atrial extrasystole so that only competent "P" waves are used in determining the average value and, hence, the atrial escape interval.

31 Claims, 3 Drawing Sheets

Microfiche Appendix Included
(1 Microfiche, 68 Pages)

METHOD AND APPARATUS FOR CALCULATING THE ATRIAL ESCAPE INTERVAL FOR A CARDIAC PACING DEVICE IN THE EVENT OF ATRIAL EXTRASYSTOLES

This specification is accompanied by a microfiche appendix including one film.

A portion of the disclosure of this patent contains material which is subject to copyright protection. The copyright owner has no objection to the facsimile reproduction by any one of the patent disclosure, as it appears in the Patent and Trademark Office patent files or records, but otherwise reserves all copyright rights whatsoever.

FIELD OF THE INVENTION

The present invention relates generally to the stimulation of the heart of a patient with the help of a dual-chamber pacemaker, more particularly to controlling atrial stimulation following a calculated atrial escape interval.

BACKGROUND OF THE INVENTION

Dual-chamber pacemaker devices have been known and used for a long time. They make it possible to regulate the cardiac activity of the ventricle by using information collected at the level of the atrium of the patient's heart in case of a failure of the atrial-ventricular conduction, which will then induce a block, at the level of the ventricles, of the response to a depolarization of the atriums.

A pacemaker of this kind detects the depolarization of an atrium through what cardiologists designate as the "P" wave, and will then stimulate the ventricle, if this ventricle has not spontaneously depolarized after a given or selected atrialventricular delay. Such a pacemaker also is capable of not stimulating the ventricle in response to "P" waves occurring at too close intervals, to avoid putting a useless or unnecessary strain on the heart.

A dual-chamber pacemaker is, in addition, capable of stimulating the atrium when there is no longer an atrial detection, i.e., a spontaneous atrial depolarization. In a manner known per se, when there is no longer an atrial detection, the pacemaker will stimulate the atrium and, after the atrialventricular delay, it will stimulate the ventricle.

At present, two methods are used in the case of such an absence of atrial detection. In one method, the heart is immediately subjected to a stimulation with a frequency equal to the basic frequency, that is, the minimum frequency which the patient's heart is able to withstand. In some cases, this involves a large change in frequency. In the other method, the stimulation is initially maintained at the stimulation frequency that existed before the absence of atrial detection, for example, for eight beats, and then the frequency is gradually reduced down to the basic frequency. U.S. Pat. No. 4,313,442 discloses a pacemaker in which the stimulation rhythm decreases gradually down to the basic frequency.

The basic frequency is defined as the largest possible value which can be assumed by an escape interval, corresponding to the time at the end of which the atrium must be compulsorily stimulated if the spontaneous depolarization thereof is not detected. This escape interval is regularly recalculated, so that its value tends to approach ever more closely the value separating two successive "P" waves.

A drawback to the known method is that any atrial event, whatever it may be, will be taken into account in the re-calculation of the atrial escape interval (AEI). In the case of frequent fast atrial rhythms, this leads to an increasingly fast rhythm.

At present, it is known to carry out this calculation by measuring the delay between two "P" waves either at each eighth cycle or after each cycle, the cycle being defined as the set of an atrial depolarization and of the next following atrial depolarization. A problem with this method is that the measurements may be made during an atrial extrasystole, that is, a premature spontaneous atrial depolarization. In such case, the delay between the two successive "P" waves is abnormally short. This results in the calculation of a short atrial escape interval and an accelerated stimulation of the atrium, which tends to stimulate the heart at an uselessly high frequency, in the case of an absence of atrial detection.

There is thus a continuing need to provide improved methods for stimulating a patient's heart, particularly the atrium, at appropriate times and rates.

SUMMARY OF THE INVENTION

It is, therefore, an object of the present invention to provide for calculating an atrial escape interval that minimizes the likelihood that an atrial extrasystole will influence the calculation. It is another object to provide an atrial escape interval that reflects more accurately the patient's physiological condition.

Accordingly, one aspect of the present invention provides a method for calculating the escape interval at the end of which the atrium of a heart must be stimulated in case of a lack of spontaneous depolarization, characterized by calculating the atrial escape interval as a function of the average value of the delays between two "P" waves measured over a number of cardiac cycles selected from between 2 and 12, more preferably 8, such that only those cardiac cycles which present no atrial extrasystole are taken into account in determining the atrial escape interval. In one embodiment, the calculated average value is taken as the value of the atrial escape interval.

In a preferred embodiment of the invention, a post-atrial atrial refractory period (PAARP) is selected and triggered after every atrial depolarization. Then, every following "P" wave that is detected during a PAARP is interpreted as corresponding to an extrasystole. If a "P" wave is determined to correspond an atrial extrasystole, there is no triggering of the selected atrial-ventricular delay, and instead a new atrial escape interval is triggered, thereby to avoid a too fast stimulation of the ventricle. In this embodiment, the occurrence of a "P" wave during the PAARP indicates that the cardiac cycle comprises an atrial extrasystole. Accordingly that cardiac cycle and the P—P delay interval for that cycle are not used in recalculating the atrial escape interval.

Preferably, the selected PAARP has a duration equal to a fraction or a percent of the time separating two "P" waves, without exceeding a selected programmable maximum delay. For example, the fraction may be selected to be greater than 50%, preferably between and 80%, and more preferably 75%, and the programmable maximum delay is selected in the range between 300 and 700 milliseconds, more preferably 560 milliseconds (ms).

Another aspect of this invention is directed towards an apparatus for calculating an atrial escape interval for a cardiac pulse generator having a sensor for monitoring atrial depolarization as P waves and electrodes for stimulating atrium and ventricular depolarization. One such apparatus includes:

- a filter for discriminating P waves corresponding to physiological depolarization from P waves corresponding to atrial extrasystoles;
- a circuit for determining the period of time by which a P wave corresponding to a physiological depolarization follows a preceding P wave;
- means for accumulating the determined delays for a plurality of cardiac cycles which do not present an atrial extrasystole, the plurality being selected from between 2 and 12 cycles; and
- a means for selecting an atrial escape interval as the average of the accumulated delays.

The filter is preferably a post-atrial atrial refractory period triggered by a preceding P, wave during which a following P wave detected is interpreted as corresponding to an atrial extrasystole. In one alternate embodiment, the atrial escape interval is calculated as a function of the average determined delays. Preferably, the determining means determines a time between successive physiological P wave.

The apparatus also may include a counter for counting the number of consecutive atrial stimulations and a circuit for incrementing the atrial escape interval by an amount selected from between 16 ms and 94 ms, up to a maximum interval corresponding to the basic frequency, in response to the counter reaching a preselected number of from between 4 and 12, preferably 8, consecutive atrial stimulations. In the absence of an atrial stimulation, the PAARP is preferably recalculated to be either (1) a first percent of the delay between the last two P waves not corresponding to an atrial extrasystole in response to the last P wave corresponding an extrasytole or (2) a second percent (preferably the same as the first percent) of the average determined delay in response to the occurrence of a P wave corresponding to an atrial extrasystole. Following an atrial stimulation, the PAARP is preferably recalculated to be a third percent (preferably the same as the first percent) of the existing atrial escape interval. In the latter case, the atrial escape interval is maintained constant unless the selected number of consecutive atrial stimulations have occurred, in which case the atrial escape interval is incremented.

BRIEF DESCRIPTION OF THE DRAWINGS

Further features will emerge from the appended drawings in which like reference characters refer to like elements and in which.

DETAILED DESCRIPTION OF THE INVENTION

Figure 1:
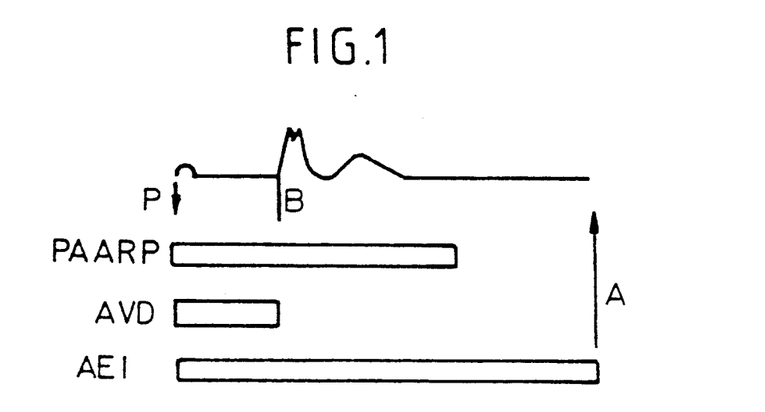
FIGS. 1 and 2 are diagrams illustrating how the method for calculating the atrial escape interval in accordance with an embodiment of the present invention in the absence and the presence of an atrial extrasystole, respectively.
Figure 2:
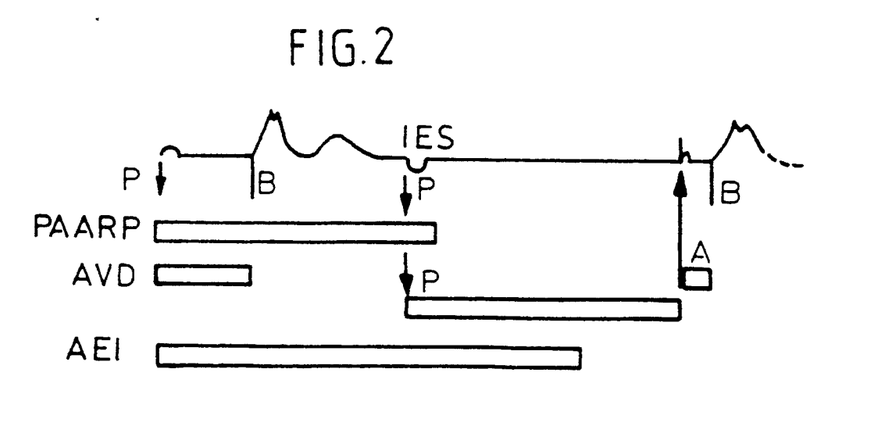
Figure 3:
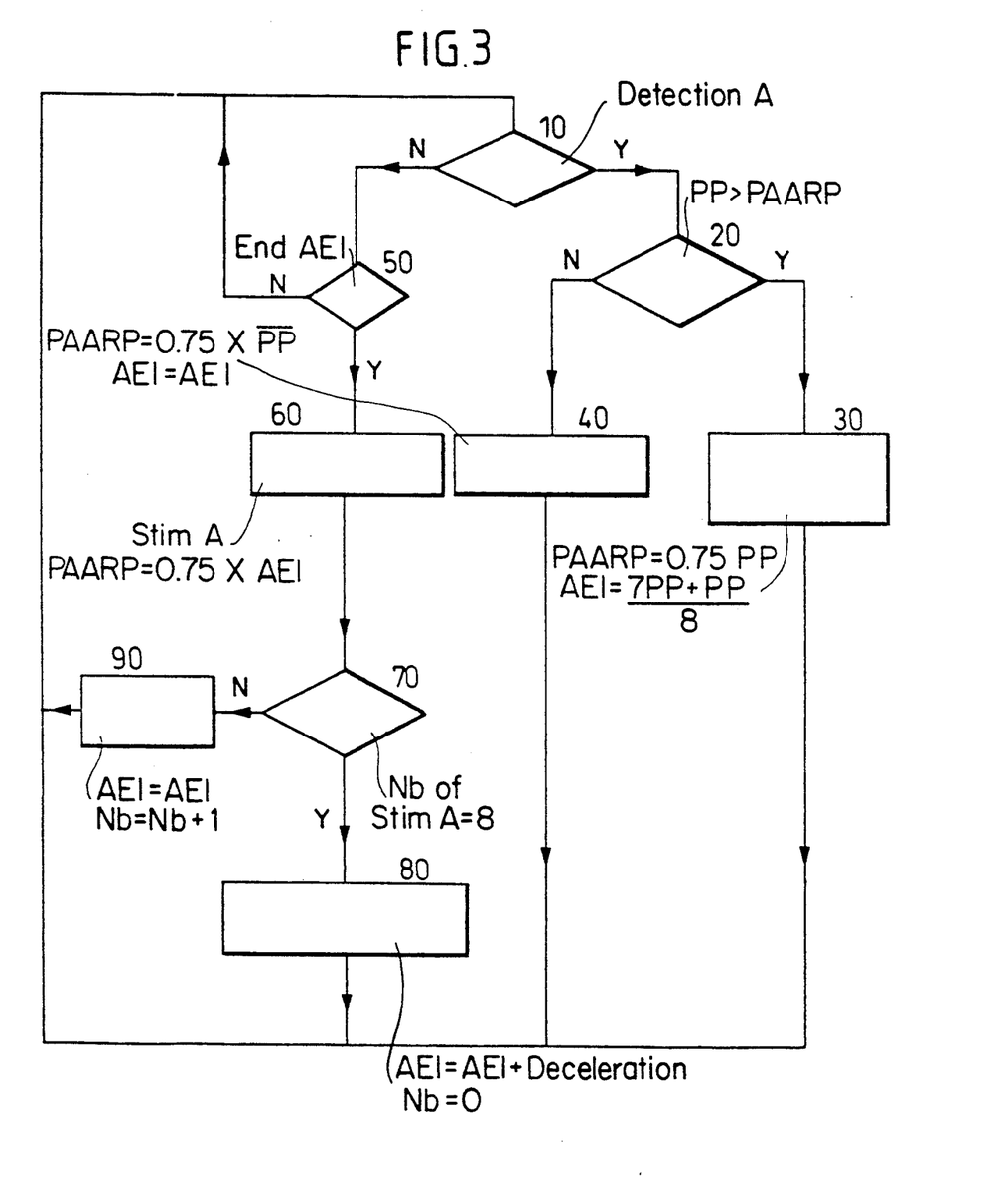
FIG. 3 is a flow chart diagram of the operation of a pacemaker according to a preferred embodiment of the invention.

Referring to FIGS. 1-3, a preferred embodiment of the invention is shown. The method of the invention provides for calculating an average value of the delay between two successive "P" waves, on the basis of measurements taken over a number of heart cycles selected from between 2 and 12, more preferably 8, which number of cycles do not present an atrial extrasystole.

For carrying out this method, it is preferred to use a cardiac pulse generator, e.g., a dual chamber pacemaker, capable of determining whether an acceleration of the heart rhythm is physiological or pathological. The acceleration is considered physiological when the patient is in a phase of more or less prolonged effort whereas it is considered pathological in presence of atrial extrasystoles. Appropriate pacemaker operating modes include, without limitation, DDD and VDD.

To implement the invention, there is defined a very short absolute refractory period after a stimulation of the ventricle during which no event is detected in the atrium. This period is limited to the recovery time needed by the signal sensing and processing amplifiers of the pacemaker following the stimulation. For example, a period of 110 msec may be used. This short absolute refractory period makes it possible to improve the sensing time at the level of the atrium and to examine a maximum number of accelerations of the heart rhythm, in order to determine whether a sensed acceleration is the result of the patient's physical effort or an atrial extrasystole.

In accordance with the invention, and referring to FIGS. 1 and 2, there are defined a post-atrial atrial refractory period (PAARP) and an atrial escape interval ("AEI"). The shorter, downwardly pointing arrows P represent the occurrence of a P wave in the sensed cardiac cycle, which represents the atrial depolarization event and triggers the PAARP and the AEI intervals, and also may trigger the atrial-ventricular delay (AVD). The sensed ventricular depolarization event is represented by the vertical line B.

The value of the PAARP is selected to be a fraction of the average time separating two "P" waves. Preferably, the fraction is equal to 75% of the time separating the two "P" waves of the previous cycle, without exceeding a programmable delay which may be selected from between 300 and 700 ms, more preferably 560 ms. The programmable delay is preferably selected to initialize the P—P interval after which the successive P waves are counted automatically; 560 ms is a default value that is used if no other value is programmed. In selecting the fraction, it is noted that it is considered that a physiological acceleration is never capable of generating a "P" wave with an acceleration exceeding 25%, i.e., that the time delay of the accelerating "P" wave is less than 25% of the delay of the preceding cycle.

A pacemaker operating in accordance with the present invention thus will refuse to take into account a "P" wave occurring before the end of the determined PAARP which is triggered by the detection of a preceding "P" wave. When such a "P" wave occurs within this delay (see FIG. 2), it is interpreted as being an isolated extrasystole (IES), a pathological event. In response, the pacemaker will trigger a new atrial escape interval. At the end of the new atrial escape interval, the pacemaker will stimulate the atrium and, after expiration of the selected atrial-ventricular delay, stimulate the ventricle, if necessary. The atrial-ventricular delay may be selected in a conventional manner. Other values may be used as appropriate for, for example, a present minimum or in accordance with a calculated value, which selection is not pertinent to this invention. It is noted that the Figures are not drawn to scale.

Accordingly, by observing whether a "P" wave has been detected within or not within the PAARP, one can determine whether or not an atrial extrasystole has taken place during the cycle. Thus, cycles presenting an atrial extrasystole can be rejected and only the delays between the successive competent "P" waves are used in calculating the atrial escape interval. The term "competent "P" wave" refers to a "P" wave which can be effectively followed by a stimulation of the ventricle. Thus, the PAARP is used as a filter for discriminating valid physiological P waves from undesirable pathological P waves.

According to the present invention, the delay between two "P" waves is measured solely when the "P" waves are competent. This will be done each time over the selected number of cycles, e.g., eight cycles. There is then calculated the average of these eight values, which are taken as the value of the delay between two "P" waves. This value is then compared to the value of the existing atrial escape interval.

When the existing atrial escape interval is longer than the delay between two "P" waves, the escape interval is then equal to the average of those eight values reduced by a value selected from between 16 and 94 ms, preferably 47 ms, in order to stimulate the heart at a rhythm taking into account a possible acceleration of the patient's physiological activity. The selected value is preferably programmed.

When the atrium has been stimulated for a certain number of cycles, for example, between 4 and 12 cycles, more preferably 8 cycles, the atrial escape interval is prolonged by a value selected from between 16 and 94 ms, more preferably 47 ms, until the resulting atrial escape interval corresponds to the programmed basic frequency. Thus, the stimulation rate will gradually reduce to the basic frequency.

Advantageously, the present invention provides an improved correlation and response between the cardiac activity and the patient's activity when a lack of atrial depolarization is detected.

With reference to FIG. 3, the following abbreviations are used in describing a preferred embodiment of the method of the present invention: "Detection A" refers to atrial detection; End of AEI" refers to the end of the atrial escape interval; "Stim A" refers to an atrial stimulation; "Nb of Stim A" refers to the number of atrial stimulations during consecutive cycles; "Deceleration" refers to the extension of the AEI by 47 ms; "Nb=0" refers to resetting to zero of the stimulations counter; "PP" refers to the interval between two "P" waves; "$\overline{PP}$" refers to the average of the PP intervals over 8 cycles; "Y" refers to yes; and "N" refers to no.

With reference to FIG. 3, a preferred embodiment of the invention is as follows. The atrial detection is monitored at box 10. If an atrial detection occurs, the PP interval is compared to the PAARP interval at box 20. If the PP interval exceeds the PAARP interval, the PAARP and IEA intervals are adjusted at box 30 such that the PRAAP is selected to be 75% of the PP interval just calculated, and the IEA is selected to be the average of the seven prior calculated PP intervals and the just calculated PP interval. At this point, the method returns to box 10. If the PP interval is less than the PRAAP interval, then at box 40, the PRAAP interval is selected to be 75% of the existing $\overline{PP}$ and the IEA interval is selected to be the existing IEA, whereupon the method returns to box 10. The $\overline{PP}$ interval is created and updated as new PP intervals are acquired. Only competent P waves are used.

If, instead, no atrial detection is sensed at box 10, the last triggered AEI is investigated at box 50 to determine whether or not the AEI interval has expired. If it has not expired, the method returns to box 10. If it has expired, the pacemaker stimulates the atrium at box 60 and selects the PAARP interval to be 75% of the AEI. Thereafter, the method determines whether eight atrial stimulations occurred during consecutive cardiac cycles at box 70, e.g., using a counter that is successively incremented by successive atrial stimulations. If eight stimulations have occurred, then at box 80 the number of cardiac cycles counted is reset to zero and the AEI is extended, i.e. increased, by the preselected time, e.g., 47 ms up to the maximum time. If eight consecutive atrial stimulations have not occurred, than at box 90 the AEI is maintained the same and the atrial stimulation counter is incremented by one. The method then returns to box 10. It is understood that box 10 and box 50 provide a processing loop, waiting for either an atrial detection or the end of the last triggered atrial escape interval before proceeding.

The method of the invention is preferably performed by a computer, more preferably, a microprocessor device having software instructions in an associated memory device and sensors suitable for performing the measurements described and providing stimulating pulses as indicated including, without limitation, a microprocessor controlled dual chamber pacemaker having input parameters programmable for the patient's characteristics, in the known manner. Appropriate devices for converting analog circuit signals to digital signals and vice versa may be provided. It is to be understood, however, that the method also may be performed by analog circuit devices, and by a combination of digital and analog circuits. All of the foregoing components are conventional.

Figure 4:
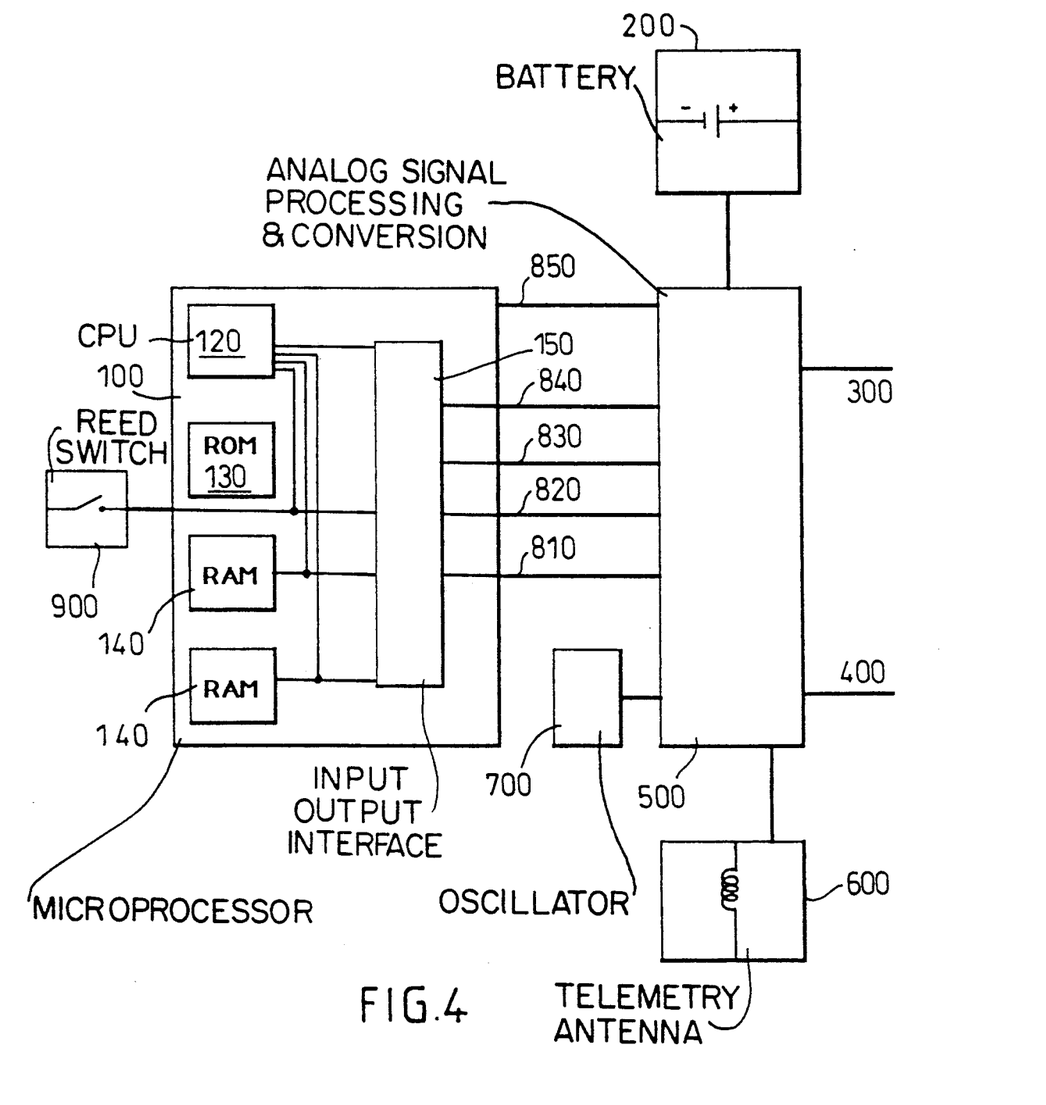
FIG. 4 is a block schematic diagram of the apparatus of the invention.

Referring to FIG. 4, a schematic embodiment of a dual chambered pacemaker in accordance with the present invention is illustrated. The apparatus includes a microprocessor 100, a battery 200, an atrial sensing and stimulating catheter 300, a ventricular sensing and stimulating catheter 400, an analog signal acquisition and conversion circuit 500, a telemetry antenna 600 and an associated reed switch 900, a clock oscillator 700 and appropriate data and control buses.

Microprocessor 100 is preferably an eight bit device including a central processing unit 120, a ROM-type memory device 130 which includes software instructions for operating the pacemaker including inter alia in accordance with the present invention, one or more RAM-type memory devices 140 for data storage, manipulation and other memory related functions, and an input/output interface 150 for communicating within microprocessor 100 and between microprocessor 100 and other components of the pacemaker. Input/output interface 150 includes, for example, a data bus 810 for data transmission, an address bus 820, a control bus 830, all of which are conventional and dependent on the microprocessor device used.

Catheters 300 and 400 are conventional pacemaker catheter electrodes and preferably have associated conventional protection circuits (not shown) to protect the pacemaker and patients from external signals in the usual manner.

Circuit 500 provides for converting analog cardiac atrial and ventricular signals to digital signals (and for converting digital signals to analog signals) for signal processing by microprocessor 100, and does not itself form any part of the present invention.

Antenna 600 is used for remote programming of microprocessor 100 in cooperation with actuation reed switch 900, in the conventional manner. Antenna 600 also may be provided with suitable protection circuits. Oscillator 700 provides the base clock frequency for operating the data acquisition and processing functions. The foregoing components are available in one form or another and may be assembled by a person of ordinary skill in the art.

A preferred microprocessor controlled dual chamber pacemaker for use with the present invention is an atrial based pacemaker such as the model CHORUS II TM, implantable dual chamber pulse generator DDD MO, available from Ela Medical, Montrouge, France. The model CHORUS II 6200 Series, specifically the 6234, includes an operating mode that uses the present invention when the "lissage" or smoothing algorithm is programmed on.

Set forth below and with reference to the software in the appendix, several signal processing routines in accordance with a preferred embodiment of the invention are described. In the following description, the use of quotation marks indicate a software variable that is a preset or programmable value, a calculated value based on sensed measurements or a software counter or flag, and the use of uppercase letters indicate measured parameters of cardiac activity. Also, the use of the back to back less than greater than symbols < > before a parameter X refers to not X. The software contains program instructions and parameters in addition to those that pertain to the present invention, which place the use of the invention in context.

Routine "Table VV" is implemented to update a sliding average of the time between ventricular events, i.e., V—V intervals, which occurs when the preset invention is utilized. The term "asso mode" is a state variable for the pacemaker operating condition and the term ASSO is a state where the atrium and ventricle are controlled in association in response to the occurrence of competant P waves. The term "flag atr cycle" is a flag for the atrium cycle which may be based on ventricle events, VV, atrial events, PP or both. The flag may be set to save VV intervals and/or PP intervals. The term "prg smoothing esc increase" is a flag that refers to using smoothing algorithm of the the present invention if set to "< >off" (i.e., not off or on) or not using the preset invention if set to off. The term "global mode" is a programmable term for configuring the pacemaker and, for the present invention, is set to be NORM. Routine "Table VV" is as follows:

```
IF
    AND
        "global mode" = NORM
        OR ; < 2
            "flag atr cycle" = SAV VV
            "flag atr cycle" = SAVE PP & VV
        RO
```

-continued
```
    OR
        "asso mode" < > ASSO
        "prg smoothing esc int increase" < > OFF
    RO
    DNA
THEN
    "sum 8 VV" = "sum 8 VV" + "time between last cycle starts"
                  − "table VV("VV ptr")"
    "aver 8 VV" = "sum 8 VV"/8
    "table VV("VV ptr")" = "time between last cycle starts"
    "VV ptr" = ("VV ptr" + 1) mod 8
ELSE
FI
```

In the present invention, when the "flag atr cycle" is set to save VV, "table VV" is updated when the pacemaker is in the ASSO state, and when the pacemaker is in a fallback mode or ascending mode, i.e., where the atrial and ventricular events are not associated and the ventricular rate either is being decreased to a basic rate or increased to correspond to the existing atrial rate, respectively. When the pacemaker is in the fallback or ascending mode, the VV interval may be used to calculate smoothing the escape interval, for example, when no PP interval is obtained. When the "flag atr cycle" is set to SAVE PP & VV, the "table VV" is updated only when the pacemaker is in the fallback or ascending modes, where the VV interval may be used to calculate the escape interval. However, when "flag atr cycle" is set to SAVE PP, "table VV" is not updated.

The routine CALCUL DE "ESC INT SMOOTHED" is implemented to calculate the variable "esc int smoothed" whatever the mode of association may be and is modified by the following:

(1) Telemetry, in which reprogramming is required, such that the variable "command executed" is set to a default or nominal value, or to a programmed value, where the variable "esc int smoothed" is initially equal to the period corresponding to the programmed base rate (the term "prg bas per") upon turning off the smoothing algorithm by telemetry reprogramming of the pacemaker, and (2) Retrograde P Search, in which one is supposed to have detected the retrograde P wave, i.e., a P wave corresponding to an atrial extraystole, where the variable "esc int smoothed" is initially set equal to "prg bas per"

The following additional terms are defined. The term "min per" is the minimum period corresponding to the maximum ventricular pacing frequency programmed for the patient and the terms "aver 8 PP" and "aver 8 VV" refer to the average of 8 PP ad VV intervals, respectively. The term "prg smoothing esc int increases" refers to the programmable time period for incrementing the escapt interval, e.g., 47 msec. The routine is as follows:

```
IF; smoothing on
    "prg smoothing esc int increase" < > OFF ; < > 0
THEN; calculate esc int smoothed gain
    IF
        OR
            "flag atr cycle" = SAVE VV
            "flag atr cycle" = SAVE PP & VV
        RO
        THEN
            "temp" = "aver 8 VV"
        ELSE
            "temp" = "aver 8 PP"
        FI
    IF
```

```
                                -continued
        "temp" + "prg smoothing esc int increase" > "esc int
smoothed
    THEN "prg smoothing esc int increase" to "esc int smoothed"
        add
    ELSE
        "esc int smoothed" = "temp" +" prg smoothing esc int
        increase"
    FI
    IF
        "esc int smoothed" < "min per"
    THEN
        "esc int smoothed" = "min per"
    ELSE
        IF
            "esc int smoothed" > "prg bas per"
        THEN
            "esc int smoothed" = "prg bas per"
        ELSE
        FI
    FI
ELSE
FI
```

The routines UPDATE "table PP" & "prapa" CASE P WAVE and UPDATE" "Table PP" & PRAPA CASE A PACE refer to updating the table PP of the sliding average of PP intervals and to updating the PAARP interval in response to competent P waves in response to atrial detection and atrial pacing, respectively. The term "cycle post-=ESV state" refers to the cardiac cycle after the absence of an atrial event in the ventricular cycle, the term "flag no asso" refers to synchronous ventricular event, the term "time flow" refers to the time since the last ventricular event, the term "prapa time" refers to the time at which the triggered PAARP interval will end, the term "time between last AV start" refers to the elapsed time since the last P wave, the term "last PP" refers to the last determined PP interval based on competent P waves, the term "flap P in prapa" refers to a flag that is set when a P wave occurs before the end of the PAARP interval triggered by a preceding P wave, the term "xprg percent prematurity" refers to the percent used in calculating new PAARP, e.g., 75%, the term "prapa" refers to a PAARP, the term "xprg prapa max" refers to a programmed maximum PAARP; The term "V DESYNC A" refers to the ventricle and atrial events being asynchronous.

The Routines are as follows:

```
UPDATE "table PP" & "prapa" CASE P WAVE
IF ;
    AND
        "global mode" = NORM
        OR ; >= 1
            "flag atr cycle" = SAVE PP
            "flag atr cycle" = SAVE PP & VV
        RO
        "cycle post-ESV state" = NONE
    DNA
THEN
    IF AND
            "flag no asso" = 0
            "flag P in prapa" = 0
            "time now" > "prapa time"
        DNA
    THEN
        IF
            "time between last AV starts" <= 1.5* "last PP"
        THEN
            "update table PP (Q.2)
            "last PP" = "time between last AV starts"
            ""temp" = "last PP"
        ELSE
            IF
                    "asso mode" = ASSO
                THEN
                    update table PP (Q.2)
                    "last PP" = "time between last AV starts"
                    "temp" = "aver 8 PP"
                ELSE
                    "temp" = "last PP"
                FI
            FI
        ELSE
            "temp" = "aver 8 PP"
        FI
        CALC "prapa" & SET "prapa time" (Q.1)
ELSE
FI
Q.1 CALC PRAPA & SET Prapa time
"prapa" = (1-"xprg percent prematurity")*"temp"
IF    "prapa" >= "xprg prapa max"
THEN
    "prapa" = xprg prapa max"
ELSE
FI
"prapa time" = "time now" + "prapa"
Q.2 update table PP
"sum 8 PP" = "sum 8 PP" + "time between last AV starts"
                        —"table PP ("PP ptr")"
"aver 8 PP" = "sum 8 PP"/8
"table PP" ("PP ptr")" = "time between last AV starts"
"PP ptr" = ("PP ptr" +1) mod 8
UPDATE "table PP" & PRAPA CASE A PACE
IF    AND
        "global mode" = NORM
        OR ; >=1
            "flag atr cycle" = SAVE PP
            "flag atr cycle" = SAVE PP & VV
        RO
        "cycle post-ESV state" = NONE or A & V DESYNC A
    DNA
THEN
    IF AND
            "flag no asso" = 0
            "flag P in prapa" = 0
        DNA
    THEN
        IF    "asso mode" = ASSO
        THEN
            update table PP (Q.2)
            "last PP" = "time between last AV starts"
            "temp" = "aver 8 PP"
        ELSE
            "temp" = "last PP"
        IF
            "time between last AV starts" <= 1.5* "last PP"
        THEN
            update table PP (Q.2)
        ELSE
        FI
    FI
    ELSE
        "temp" = "aver 8 PP"
    FI
    CALC "prapa" & SET "prapa time" (Q.1)
ELSE
FI
```

A preferred embodiment of a software program useful for controlling a microprocessor controlled dual-chambered pacemaker in accordance with the present invention is set forth in the microfiche appendix.

Preparation of alternate suitable software for controlling such microprocessor controlled pacemakers, and for reprogramming known microprocessor controlled dual chamber pacemaker devices, to operate in accordance with the present invention is believed to be well within the ability of a person of ordinary skill in the art.

One skilled in the art will appreciate that the present invention can be practiced by other than the described embodiments which we presented for purposes of illustration and not of limitation.

We claim:

1. A method for calculating an atrial escape interval at the end of which the atrium of a heart must be stimulated in case of a lack of depolarization, characterized by:
   detecting the occurrence of a P wave;
   determining a time delay between the P waves corresponding to a cardiac cycle;
   determining whether or not a cardiac cycle presents an atrial extrasystole;
   calculating the average value of the delays between two P waves measured over a number of cardiac cycles which do not present an atrial extrasystole and selecting said number of cardiac cycles from between 2 and 12; and
   determining the value of the atrial escape interval to be equal to the calculated average value.

2. A method according to claim 1, further characterized by triggering a post-atrial atrial refractory period (PAARP) after every detected P wave and interpreting every P wave detected during a PAARP as representing an extrasystole in the cardiac cycle.

3. A method according to claim 2, further characterized by providing a preselected time period and a fraction, calculating the PAARP value to the lesser of one of the provided fraction of the determined delay separating two P waves and the preselected time period.

4. A method according to claim 3, characterized by providing the fraction from between 0.7 and 0.8, and the preselected time period from between 300 and 700 ms.

5. A method according to claim 4 characterized in that the fraction is 0.75 and the preselected time period is 560 ms.

6. A method according to claim 3, further characterized by triggering an atrial ventricular delay in response to a detected P wave that is not interpreted to represent an atrial extrasystole, and triggering a new atrial escape interval in response to each detected P wave.

7. A method according to claim 2, further characterized by triggering an atrial ventricular delay in response to a detected P wave that is not interpreted to represent an atrial extrasystole, and triggering a new atrial escape interval in response to each detected P wave.

8. A method for adjusting the atrial escape interval of a cardiac pacing device for stimulating the atrium, comprising the steps of:
   (a) providing an initial atrial escape interval;
   (b) sensing the occurrence of a P wave representing an atrial depolarization;
   (c) determining whether or not sensed P wave is competent;
   (d) determining the delay between successive competent P waves;
   (e) selecting a plurality of cardiac cycles from between 2 and 12 cycles and calculating an average of the determined delays for the plurality of cardiac cycles; and
   (f) calculating the atrial escape interval as a function of the calculated average determined delay.

9. The method of claim 8 wherein step (f) further comprises:
   providing a maximum atrial escape interval corresponding to a basic stimulation frequency and providing a threshold number from between 4 and 12;
   monitoring the occurrence of an atrial stimulation following the atrial escape interval;
   counting the number of consecutive atrial stimulations;
   determining when the counted number is at the threshold number;
   comparing the atrial escape interval to the maximum atrial escape interval; and
   selecting a period from between 16 and 94 ms and incrementing the atrial escape interval by the selected period up to the maximum atrial escape interval in response to the counted number of consecutive atrial stimulations being at the threshold number, and not incrementing the atrial escape interval in response to the counted number of consecutive atrial stimulations being less than the threshold number.

10. The method of claim 9 wherein the threshold number of consecutive atrial stimulations is 8.

11. The method of claim 8 wherein step (f) further comprises calculating the atrial escape interval to be equal to the calculated average determined delay.

12. A method of claim 11 wherein step (e) further comprises selecting the plurality of cycles to be 8 cardiac cycles.

13. The method of claim 11 wherein step (e) further comprises selecting the plurality of cycles to be consecutive preceding cardiac cycles.

14. The method of claim 8 wherein step (c) further comprises:
   (g) calculating a post-atrial atrial refractory period (PAARP) as a percentage of the determined delay between preceding successive competent P waves;
   (h) triggering the PAARP in response to the occurrence of a first detected P wave; and
   (i) determining a detected P wave following the first detected P wave to be a competent P wave in response to the following P wave occurring after the end of the PAARP; and determining said following detected P wave to correspond to an atrial extrasystole in response to detecting the following P wave before the end of the PAARP.

15. The method of claim 14 further comprising selecting a first percentage and a second percentage, recalculating the PAARP to be one of the first percentage of the delay between the first detected P wave and the following detected P wave in response to the following detected P wave being identified as a competent P wave, and the second percentage of the calculated average determined delay in response to the following detected P wave being identified as corresponding to an atrial extrasystole.

16. The method of claim 14 wherein step (e) further comprises calculating the averaged determined delay based on the determined delay corresponding to the following P wave the detected P waves of preceding cardiac cycles and step (f) further comprises calculating the atrial escape interval to be equal to the calculated determined delay in response to the following detected P wave being determined to be a competent P wave.

17. The method of claim 14 wherein the method further comprises:
   starting the atrial escape interval in response to the occurrence of a detected P wave;
   monitoring the occurrence of P waves during the atrial escape interval;
   stimulating the atrium at the end of the calculated atrial escape interval in the absence of a detected P wave corresponding to a spontaneous atrial depolarization;

selecting a third percentage value and recalculating the PAARP to be the third selected percentage of the existing atrial escape interval;

selecting a threshold number from between 4 and 12;

counting the number of consecutive atrial stimulations; and incrementing the atrial escape interval in response to the counted number of consecutive atrial stimulations reaching the threshold number.

18. The method of claim 17 wherein the incrementing further comprises:

providing a maximum atrial escape interval corresponding to a basic stimulation frequency;

comparing the atrial escape interval to the maximum atrial escape interval; and selecting a period of from between 16 and 94 ms and incrementing the atrial escape interval by the selected period up to the maximum atrial escape interval.

19. The method of claim 18 wherein the step of selecting the threshold number further comprises selecting the threshold number to be eight.

20. Apparatus for adjusting an atrial escape interval for use in a cardiac pacing comprising:

a sensor for monitoring cardiac electrical activity including the occurrence of the P waves corresponding to atrial depolarization and atrial stimulation;

means for providing an initial atrial escape interval following a detected P wave;

a filter for determining whether a sensed P wave is competent or corresponds to an atrial extrasystole;

a timer for determining the delay between successive competent P waves;

processing means for selecting a plurality of cardiac cycles from between 2 and 12 cycles and calculating an average of the determined delays for the plurality of cardiac cycles; and means for adjusting the atrial escape interval as a function of the calculated average determined delay.

21. The apparatus of claim 20 further comprising means for providing a maximum atrial escape interval corresponding to a basic frequency, means for providing a threshold number selected from between 4 and 12, means for providing a period selected from between 16 and 94 ms, a counter for counting the number of consecutive atrial stimulations following an atrial escape interval, and means for comparing the counted number to the threshold number wherein the adjusting means further comprises means for incrementing the atrial escape interval by the period up to the maximum atrial escape interval in response to the counted number of consecutive atrial stimulations reaching the threshold number.

22. The apparatus of claim 21 wherein the selected threshold number of consecutive atrial stimulations is 8.

23. The apparatus of claim 20 wherein the adjusting means sets the atrial escape interval equal to the calculated average determined delay.

24. The apparatus of claim 23 wherein the processing means selects 8 cardiac cycles.

25. The apparatus of claim 23 wherein the processing means calculates the average determined delay based on consecutive preceding cardiac cycles.

26. The apparatus of claim 20 wherein the filter further comprises a post-atrial atrial refractory period (PAARP) having an interval that is a percentage of the determined delay between preceding successive competent P waves;

means for starting the PAARP in response to the occurrence of a first P wave; and discriminating means for determining whether a sensed following P wave occurs during or after PAARP such that the P wave is competent if it occurs after the end of the PAARP and corresponds to an atrial extrasystole if it occurs before the end of the PAARP.

27. The apparatus of claim 26 further comprising means for recalculating the PAARP to be one of a first selected percentage of the delay between a first P wave and the following P wave in response to the following P wave being a competent P wave, and a second selected percentage of the calculated average determined delay in response to the following P wave corresponding to an atrial extrasystole.

28. The apparatus of claim 26 further comprising means for recalculating the atrial escape interval to be equal to the calculated determined delay in response to the following P wave being a competent P wave, wherein said average determined delay comprises the determined delay corresponding to the following P wave and preceding cardiac cycles.

29. The apparatus of claim 26 further comprising:

means for triggering the atrial escape interval in response to the occurrence of a P wave;

means for recalculating the PAARP to be a third selected percentage of the existing atrial escape interval in response to a stimulation of the atrium following a triggering atrial escape interval; and a counter for counting the number of consecutive atrial stimulations and a means for providing a threshold number selected from between 4 and 12 and comparing the counted number to the threshold number, wherein the means for recalculating the atrial escape interval increments the atrial escape interval in response to the counted number of consecutive atrial stimulations being the same as the threshold number.

30. The apparatus of claim 29 further comprising means for providing an interval selected from between 16 and 94 ms and a means for providing a maximum atrial escape interval corresponding to a basic frequency, wherein the means for recalculating the atrial escape interval increments the atrial escape interval by the selected interval up to the maximum atrial escape interval.

31. The apparatus of claim 30 wherein the selected threshold number is eight.

* * * * *